(12) United States Patent
Kong

(10) Patent No.: US 7,754,327 B2
(45) Date of Patent: Jul. 13, 2010

(54) ABSORBENT ARTICLES COMPRISING A RADIATION CURED HOT MELT POSITIONING ADHESIVE

(75) Inventor: Wei Kong, Slough (GB)

(73) Assignee: Henkel AG & Co. KGaA, Duesseldorf (DE)

(*) Notice: Subject to any disclaimer, the term of this patent is extended or adjusted under 35 U.S.C. 154(b) by 430 days.

(21) Appl. No.: 11/432,007

(22) Filed: May 11, 2006

(65) Prior Publication Data

US 2007/0264497 A1 Nov. 15, 2007

(51) Int. Cl.
B32B 7/12 (2006.01)
C08F 2/50 (2006.01)

(52) U.S. Cl. .................. 428/345; 522/35; 522/904; 522/905; 522/109; 428/355 AC

(58) Field of Classification Search ............. 522/35, 522/904, 905, 109; 428/345, 343, 349, 355 R, 428/355 AC
See application file for complete search history.

(56) References Cited

U.S. PATENT DOCUMENTS

| 4,376,440 | A | | 3/1983 | Whitehead et al. |
| 4,423,101 | A | * | 12/1983 | Willstead ............. 428/76 |
| 5,514,122 | A | * | 5/1996 | Morris et al. ............. 604/387 |
| 5,853,750 | A | | 12/1998 | Dietz et al. |
| 6,497,949 | B1 | * | 12/2002 | Hyde et al. ............. 428/355 EN |
| 6,720,399 | B2 | * | 4/2004 | Husemann et al. ............. 526/319 |
| 6,858,295 | B2 | * | 2/2005 | Diehl et al. ............. 428/343 |
| 6,926,959 | B2 | * | 8/2005 | Kroll et al. ............. 428/345 |
| 7,157,535 | B2 | * | 1/2007 | Herr et al. ............. 526/279 |
| 7,442,438 | B2 | * | 10/2008 | Boulos et al. ............. 428/355 AC |
| 2003/0199604 | A1 | | 10/2003 | Kroll et al. |
| 2003/0236425 | A1 | * | 12/2003 | Herr et al. ............. 556/443 |
| 2005/0182150 | A1 | | 8/2005 | Bamborough et al. |
| 2006/0110596 | A1 | * | 5/2006 | Palasz et al. ............. 428/355 R |
| 2006/0220596 | A1 | * | 10/2006 | Mendelsohn ............. 315/307 |

FOREIGN PATENT DOCUMENTS

EP 0342808 A 11/1989

\* cited by examiner

Primary Examiner—Susan W Berman
(74) Attorney, Agent, or Firm—James E. Piotrowski

(57) ABSTRACT

An article comprising an adhesive attachment region is provided. The adhesive attachment region comprises a radiation curable hot melt pressure sensitive adhesive.

10 Claims, 1 Drawing Sheet

ABSORBENT ARTICLES COMPRISING A RADIATION CURED HOT MELT POSITIONING ADHESIVE

FIELD OF THE INVENTION

Figure 1:
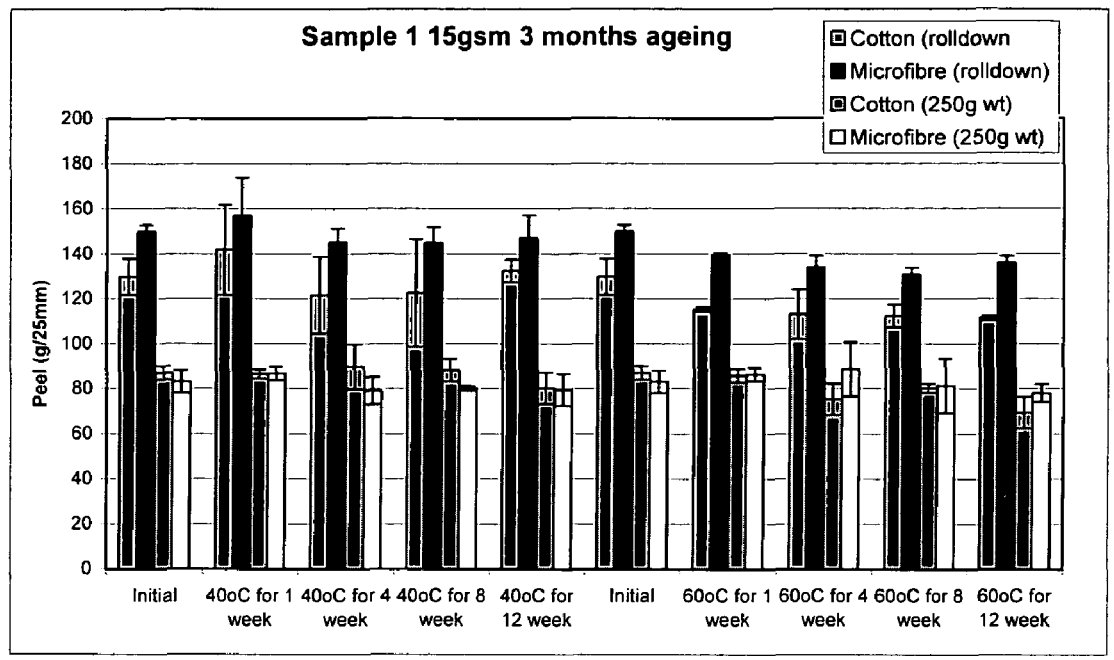

The invention relates to the use of radiation curable hot melt adhesives as positioning adhesives for absorbent articles.

BACKGROUND OF THE INVENTION

Disposable absorbent pads come in a wide variety of shapes and sizes, however, all generally employ a liquid impermeable barrier sheet coated or supplied with an adhesive attachment region.

This adhesive attachment region has traditionally been coated with a hot-melt adhesive which is protected by a release liner. The release liner is left in place to protect the adhesive from contamination or from transfer to adjacent incontinent pads or sanitary napkins or packaging materials in the package prior to use, and is removed by the user prior to attachment of the article, e.g., a sanitary napkin or adult incontinent pad, to the fabric undergarment of the user.

Hot melt adhesives based on styrene block copolymers, i.e., SIS, SBS, SEBS, SEPS, etc., or other polymers like polyolefins, for use as positioning adhesive with absorbent articles have been widely used due to the ease of applying the adhesive to desired substrates and their good positioning properties to cotton. However, with increasing trends in the market towards more fashionable undergarments made from microfibre fabrics, which give silky, stretchy and good fitness-feeling, positioning adhesives must be able to bond microfibre fabrics, as well as other fabrics, in addition to cotton, and keep the absorbent articles in position without leaving residual adhesive on the undergarment following removal of the absorbent article.

Conventional hot melt positioning adhesives, however, do not bond to microfibre fabrics well. While higher tack positioning adhesives have been developed to improve bonding to microfibre fabrics, such adhesives bond too strongly to cotton. Bonding differences observed when using conventional adhesive on different fabrics, e.g., either too little bonding to microfibre fabrics or too aggressive bonding to cotton/nylon fabrics, are unacceptable to the end users of absorbent articles.

Another concern with the use of conventional positioning adhesives is that when a more breathable PE film is used as a back sheet, low molecular ingredients of the adhesive tend to migrate into the breathable film due to the absorbency of the breathable film. This results in staining of the breathable film and significantly reduces the bonding performance of the positioning adhesive on the absorbent articles. In addition to positioning performance being significantly affected (peel can drop by 80% of its original peel value), staining is easily observed on the absorbent product by the end user and is seen as a defect in the goods.

Yet another problem encountered with the use of conventional positioning adhesives is that performance is adversely affected when the articles comprise fragrances or lotions.

There is a need in the art for a disposable absorbent article comprising a non-staining hot melt adhesive with long term stable bonding stability, and for positioning adhesives with good bonding to different fabrics and, ideally, similar bonding to different fabrics under different use conditions, and for positioning adhesives that are fragrance and lotion resistant. The current invention addresses this need in the art.

SUMMARY OF THE INVENTION

It has been discovered that radiation curable hot melt adhesives can be coated onto substrates (e.g., standard PE films, breathable PE films, and nonwoven and cloth-like back sheet materials) used in the manufacture of disposable absorbent articles such as sanitary napkins, incontinent pads, bed pads, feminine pads, panty shields, diaper inserts, etc., like standard hot melt adhesives and, when cured, exhibit excellent positioning adhesive properties. Radiation cured adhesives exhibit better bonding balance between different types of fabrics, such as cotton, microfibre fabrics and other fabrics, than do conventional rubber based positioning adhesives. Radiation cured adhesives provide stable bonding after long term aging, do not stain breathable films, and there is no transfer or adhesive residue after removal of the article from such fabrics.

The invention provides nonwoven disposable absorbent articles having an adhesive attachment region comprising a radiation cured pressure sensitive hot melt adhesive. Encompassed are articles such as sanitary napkins, incontinent pads, bed pads, feminine pads, panty shields, diaper inserts, etc. The articles will typically comprise a liquid-permeable top sheet, a liquid-impermeable back sheet, and a fluid-absorbent core material positioned between the top sheet and the back sheet. In one preferred embodiment, the back sheet is a breathable film, such as for example a breathable polyethylene film or a laminate thereof.

The invention also provides a method of manufacturing a nonwoven disposable absorbent article having an adhesive attachment region. The method comprises coating a radiation curable pressure sensitive hot melt adhesive onto a predetermined location of the article, and exposing the applied adhesive to radiant energy.

Useful adhesives will comprise a base resin and a tackifier. One preferred radiation curable adhesive comprises, as base resin, an acrylic polymer and a tackifying resin. Mixtures or blends of acrylic polymers may be used in the practice of the invention. The acrylic polymer may, desirable, be bound to a photoreactive group. In one preferred embodiment, the adhesive comprises a 2-ethylhexyl acrylate bound to a pendant benzophenone group, and a tackifier.

The radiation curable hot melt adhesive is applied to and permanently adhered to one substrate of an absorbent article such as sanitary napkins, incontinent pads, bed pads, feminine pads, panty shields, diaper inserts, etc. The cured adhesive layer is then used to attach the article to substrate, in particular a woven fabric substrate such as a supporting undergarment or bed sheet. The article can be firmly positioned to a desired location, and can be easily removed without leaving any adhesive residue.

In one embodiment of the invention, a disposable absorbent product is provided, which disposable absorbent product comprises (1) a liquid-permeable top sheet, (2) a liquid-impermeable back sheet, which top sheet may be attached to the back sheet, (3) an absorbent structure positioned between the top sheet and the back sheet, and (4) an adhesive attachment region and, optionally, a release liner.

BRIEF DESCRIPTION OF THE DRAWING FIGURES

FIG. 1 compares the ageing peel value for a radiation cured adhesive (15 gsm) on cotton and on microfibre when coated onto standard polyethylene film.

Figure 2:
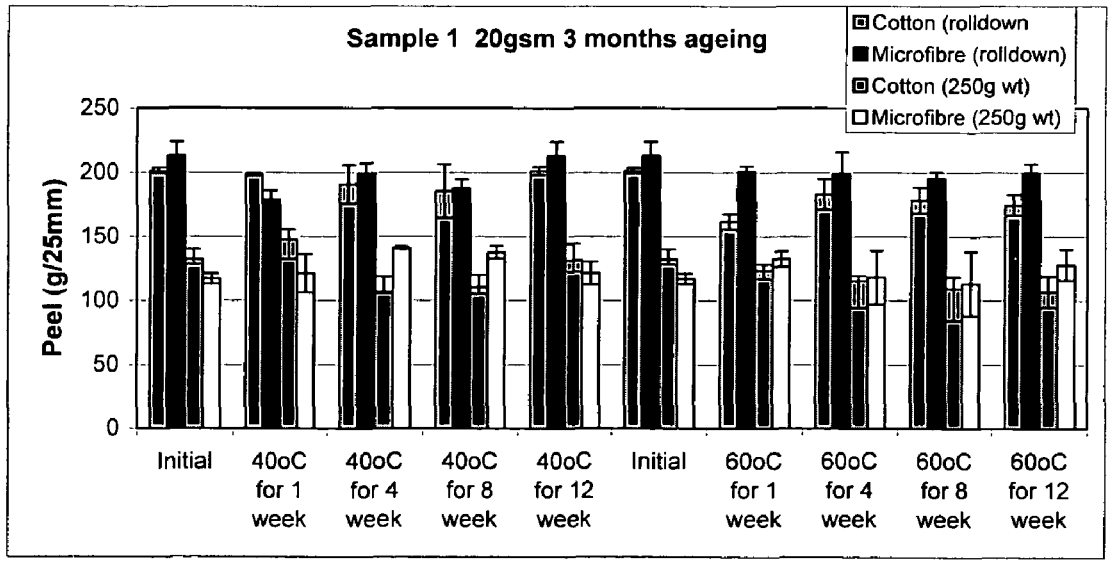

FIG. 2 compares the ageing peel value for a radiation cured adhesive (20 gsm) on cotton and on microfibre when coated onto standard polyethylene film.

DETAILED DESCRIPTION OF THE INVENTION

It has now been discovered that radiation curable pressure sensitive adhesives polymers can be used to manufacture disposable absorbent pressure sensitive adhesive articles such as sanitary napkins.

Repositionable adhesive and removable adhesive are used interchangeably herein and such terms mean that a product coated with the adhesive has sufficient adhesive strength so as to remain stationary upon the application of pressure on a surface to which it has been applied, but can be removed from the applied surface and, if desired, repositioned on the same or another surface, without adhesive residue being left on the surface.

Coat weight means the weight per unit area of adhesive coating deposited on a substrate once the coating has fully dried.

By "predetermined" position means that the article can be manufactured with the adhesive attachment region in a required or desired location for the particular end use.

The term "hot melt pressure-sensitive adhesive" or "hot melt pressure-sensitive adhesive composition" as used herein means an adhesive or adhesive composition which, upon production of adhesive goods such as disposable absorbent articles comprising an adhesive attachment region, by applying an adhesive or adhesive composition to a base material such as paper, cloth or plastic film, is capable of forming a layer of the pressure-sensitive adhesive or pressure-sensitive adhesive composition on the base material by applying it to the base material as a hot-melt.

The term "pressure-sensitive adhesive" is used herein to refer to a viscoelastic material which adheres instantaneously to most substrates with the application of slight pressure and remains permanently tacky.

The term "tackifier" as used herein means any composition which is useful to impart tack to the hot melt adhesive composition. ASTM D-1878-1T defines tack as "the property of a material which enables it to form a bond of measurable strength immediately on contact with another surface".

The term "radiation-curable adhesive" as used herein means an adhesive composition which is curable upon exposure to actinic and/or ionizing radiation. The term "radiation" is used herein to include actinic radiation such as ultraviolet radiation and ionizing radiation created by the emission of electrons or highly accelerated nuclear particles such as neutrons, alpha-particles etc.

Radiation curable adhesives useful in the practice of the invention will generally comprise a base resin, a photoinitiator and a tackifier. The term "base resin" as used herein is intended to mean a polymer which undergoes curing upon exposure to radiation.

Useful base resins include epoxidized block copolymers and/or a cycloaliphatic epoxy; an olefin (including that having a carbon-carbon double bond pendant to the backbone or on ends—such materials may be oligomeric, polymeric or monomeric and the backbone may vary in polarity ranging from aliphatic, urethane, polyester and polyether).

The adhesive will also comprise a photoinitiator, the type of which is dependent on the type of chemistry of the base resin e.g. cationic photoinitiator suitable for curing epoxidized block copolymer, cycloaliphatic epoxies, and vinyl ether olefins which includes sulfonium or iodonium salts such as SARCAT CD1010, SARCAT CD 1011 AND SARCAT CD 1012 (available from SARTOMER) (note: SARCAT CD1010 is also available under the trade name CYRACURE UVI 6974 from UNION CARBIDE). For free-radical curing systems such as olefinic or thiol-ene curing systems the following photoinitiators may be suitable: IRGACURE 651, 184 and 1700 and DAROCUR 1173, available from CIBA-GEIGY; as well as GENOCURE LBP available from RAHN; and ESACURE KIP150 available from SARTOMER. Other examples of photoinitiators which may be used include one or more of the following: benzophenone, benzyldimethyl ketal, isopropylthioxanthone, bis(2,6-dimethoxybenzoyl)(2,4,4-trimethylpentyl)phosphineoxide, 2-hydroxy-2-methyl-1-phenyl-1-propanone, diphenyl(2,4,6-trimethybenzoyl)phosphine oxides, 1-hydroxycyclohexyl phenyl ketone, 2-benzyl-2-(dimethylamino)-1-4-(4-morpholinyl)phenyl-1-butanone, alpha,alpha.-dimethoxy-alpha-phenylacetophenone, 2,2-diethoxyacetophenone, 2-methyl-1-4-(methylthio)phenyl-2-(4-morpholinyl)-1-propanone, 2-hydroxy-1-4-(hydroxyethoxy)phenyl-2-methyl-1-propanone.

One preferred radiation curable adhesive comprises, as base resin, an acrylic polymer and a tackifying resin. Mixtures or blends of acrylic polymers may be used in the practice of the invention. The acrylic polymer may, desirable, be bound to a photoreactive group (referred to herein as a UV curable acrylic polymer). A preferred polymer comprises an acrylic polymer backbone molecule that is modified with polymerized photoreactive groups, e.g., a modified benzophenone group that is chemically bonded to the acrylic polymer chain. The polymer is crosslinked by chemical grafting caused by the excitation of the photoinitiator by UV irradiation.

Particularly preferred are UV acrylic copolymers comprising a C4 to C8 alkyl acrylate and has bonded to it a pendant benzophenone group. Such UV curable polymers are commercially available from BASF under the trade name acResin® UV. These materials are solvent- and water-free acrylic raw materials that can be used for the production of pressure sensitive tapes and labels. These polymers are highly viscous liquids at room temperature and have to be heated to a temperature of about 120-130° C. to become fluid enough (viscosity ca. 40 Pa s) for the coating process on paper or plastic carriers. At this temperature, they can be applied to the backing substrate or carrier with conventional hot melt coating systems. Thus they are processed as hot melts. After being coated on the carrier, the polymer film is crosslinked by UV-irradiation to produce the adhesive properties required.

A particularly preferred UV acrylic copolymer comprises 2-ethylhexyl acrylate that has bonded to it a pendant benzophenone group. Such UV acrylic copolymers are commercially available from BASF under the trade names acResin® A 203 UV and acResin® A 204 UV. BASF's acResin® A 258 UV product, which comprises, as main component, butyl acrylate, may also be used in the practice of the invention. Another useful UV curable polymer is DS 3552X, also available commercially from BASF. The adhesives of the invention will typically comprise from about 40 wt % up to about 90 wt % of the UV-curable polymer, more preferably from about 70 to about 85 wt %.

The adhesives of the invention will preferably also comprise a compatible tackifier. By compatible tackifier is meant, as would be appreciated by the skilled artisan, a tackifier that is able to mix with adhesive polymer, e.g., acrylic polymer. Useful tackifying resins include any compatible resins or mixtures thereof such as natural and modified rosins including gum rosin, wood rosin, tall oil rosin, distilled rosin, hydrogenated rosin, dimerized rosin, and polymerized rosin; glycerol and pentaerythritol esters of natural and modified rosins, including the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natural terpenes, such as styrene/terpene and alpha methyl styrene/terpene; polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; phenolic modified terpene resins and hydrogenated derivatives thereof such, for example, as the resin product resulting from the condensation, in an acidic medium, of a bicyclic terpene and a phenol; aliphatic petroleum hydrocarbon resins resulting from the polymerization of monomers consisting primarily of olefins and diolefins; hydrogenated aliphatic petroleum hydrocarbon resins; and cyclic petroleum hydrocarbon resins and the hydrogenated derivatives thereof; also included are the cyclic or acyclic $C_5$ resins and aromatic modified acyclic or cyclic resins. Mixtures of two or more of the above described tackifying resins may be required.

In one preferred embodiment, the tackifier is a rosin based tackifier, and more specifically rosin esters and rosin acids and hydrogenated versions thereof. Examples include Foral 85 (Eastman), Pine Crystal KE 311 (Arakawa) and Staybelite Ester 10 (Hercules), as well as polyvinyl ethers, such as the Lutonal M40 grade from BASF. Other useful tackifiers include aliphatic and aromatic hydrocarbon resins, such as, for example, an alpha methyl styrene resin having a softening point of less than about 110° C. Examples include Kristalex 3085 (Kristalex F85), an alpha-methyl styrene resin having a softening point of about 85° C. which is commercially available from Eastman Chemical. Tackifiers will typically be used in amounts of up to about 40 wt % of the adhesive used, more typically from about 15 wt % to about 30 wt Useful compositions of the invention may include other additives known to those skilled in the art. These additives may include, but are not limited to, pigments, fillers, fluorescent additives, flow and leveling additives, wetting agents, surfactants, antifoaming agents, rheology modifiers, stabilizers, and antioxidants. Preferred additives are those which do not have appreciable absorption in the wavelengths of interest.

The compositions may also comprise a diluent, such as a plasticizing or extending oil including olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternatively, the oil may be totally non-aromatic. Suitable oligomers include polypropylenes, polybutenes, hydrogenated polyisoprene, hydrogenated polybutadiene, or the like having average molecular weights between about 350 and about 10,000.

The compositions may also comprise a wax, such as a petroleum derived paraffinic or microcrystalline wax (including PACEMAKER 53 available from CITGO) is useful for altering the viscosity, green-strength, reducing tack of the final composition.

Other compatible polymers may also be included, such as a block copolymer including polystyrene-polybutadiene-polystyrene, polystyrene-polyisoprene-polystyrene, poly(alpha-methyl-styrene)-polybutadiene-poly(alpha-methyl-styrene), poly(alpha-methyl-styrene)-polyisoprene-poly(alpha-methyl-styrene), as well as the hydrogenated modifications thereof, e.g. polystyrene-poly(ethylene-butylene)-polystyrene. For higher polarity systems, polymers such as polyesters (e.g. DYNAPOL materials available from HULS and sulfonated polyesters (available from EASTMAN under the title AQ series) and acrylic polymers (such as ACRONAL AC205 and ACRONAL AC 258 available from BASF) which are also reactive with free-radical systems and non-reactive acrylics (such as those available from SCHENECTADY CHEMICAL).

The adhesives used in the practice of the invention may comprise a polyolefin copolymer as an additive/filler. Use of polyolefin copolymers reduces the amount of acrylic resin required for desirable adhesive properties, thereby reducing the cost of the final adhesive formulation. Useful polymers include semicystalline or amorphous polyolefins or ethylene-containing polymers as well as blends thereof. Preferred are ethylene copolymers. The term ethylene copolymer, as used herein, refers to homopolymers, copolymers and ter- or multi-polymers of ethylene. Examples of ethylene copolymers include copolymers with one or more polar monomers which can copolymerize with ethylene, such as vinyl acetate or other vinyl esters of monocarboxylic acids, or acrylic or methacrylic acid or their esters with methanol, ethanol or other alcohols. Included are ethylene vinyl acetate, ethylene methyl acrylate, ethylene n-butyl acrylate, ethylene acrylic acid, ethylene methacrylate and mixtures and blends thereof.

Antioxidants are typically added to protect the ingredients against degradation during preparation and use of the adhesive compositions and to ensure long-term thermal stability, however without interfering with the irradiation curing of the polymer.

Combinations of antioxidants are often more effective due to the different mechanisms of degradation to which various polymers are subject. Certain hindered phenols, organo-metallic compounds, aromatic amines, aromatic phosphites, and sulphur compounds are useful for this purpose. Examples of effective types of these materials include phenolic antioxidants, thio compounds, and tris(nonylated phenyl) phosphites.

In general, up to 3% by weight of one or more antioxidants is included in the adhesive compositions. Usually, 0 to about 3 wt %, preferably from about 0.1% to about 3% by, more preferably from about 0.4% by weight to about 1.5% by weight.

Representative antioxidants that may be used in the practice of the invention include: 1,3,5-trimethyl 2,4,6-tris (3,5-di-tert-butyl-4-hydroxybenzyl) benzene; pentaerythrityl tetrakis-3(3,5-di-tert-butyl4-hydroxyphenyl)-propionate; 4,4'-methylenebis (2,6-tert-butylphenol); 4,4'-thiobis (6-tert-butyl-o-cresol); 2,6-di-tert-butylphenol; 2-t-butyl-6-(3-t-butyl-2-hydroxy-5-methylbenzyl)-4-methylphenyl acrylate, 6-(4-hydroxyphenoxy)-2,4-bis(n-octylthio)-1,2,5-triazine; di-n-octadecyl 3,5-di-tert-butyl-4-hydroxybenzyl phosphonate; 2-(n-octylthio)ethyl 3,5-di-tert-butyl-4-hydroxybenzoate; and sorbitol hexa[3-(3,5-di-tert-butyl-4-hydroxyphenyl)-propionate]. Such compounds are commercially available Ciba.

The UV curable polymer, tackifier and other desired components (e.g., antioxidant) are blended together at a temperature of from about 130° C., but not more than 150° C., until a clear mixture is formed. Entrapped air may be removed by application of a vacuum.

Following coating of the composition onto a carrier or substrate, such as a back sheet of a disposable absorbent article, it is subjected to UV irradiation. Under the action of UV light, the photoreactive groups in the UV curable polymer crosslink the polymer backbone.

Conventional H bulbs and medium pressure mercury-vapor lamps which emit UV wavelengths can be used in the practice of the invention to cure the adhesives. The acrylic polymer is curable under UV light (UV light range from UVA to UVC) and there are no harmful by-products created from the decomposition of photosensitive material so it is a safe material for skin contact application.

The radiation curable pressure sensitive hot melt adhesives described above are used in the manufacture of disposable adhesive articles. A disposable article means an article meant to be used and disposed of after one or several uses, preferable after a single use. Such articles include direct food contact labels such as informational labels attached to fresh fruit, e.g., apples, oranges and the like, price labels, resealable tabs for use in reclosure systems, e.g., tissue packages. Particularly advantageous is the use of radiation curable pressure sensitive adhesives in the manufacture of disposable absorbent articles and disposable absorbent garments.

Disposable absorbent articles refer to articles comprising a component capable of absorbing and containing a fluid, including but not limited to body fluids. Examples include bed liners and bibs as well as disposable absorbent garments. Disposable absorbent garments refer to articles designed to absorb bodily fluids, e.g., urine, menses, perspiration. Generally, such items attached to the interior surface of a supporting garment/undergarment such as underpants, shirt, bra, shoe and the like. Examples include feminine hygiene pads, incontinence pads, dress shields and nursing pads.

One aspect of the invention is directed to a disposable article comprising a pressure sensitive UV-cured acrylic adhesive. In a preferred embodiment the disposable article is a disposable absorbent article, most preferable a disposable absorbent garment having an attachment region comprising a pressure sensitive UV-cured acrylic adhesive.

A preferred embodiment of the invention is directed to a disposable absorbent article comprising a liquid-permeable top sheet, a liquid-impermeable back sheet, a fluid-absorbent core material positioned between the top sheet and the back sheet and an adhesive attachment region comprising a pressure sensitive UV-curable acrylic adhesive. In one embodiment of the invention, a disposable absorbent product is provided, which disposable absorbent product comprises (1) a liquid-permeable top sheet, (2) a liquid-impermeable back sheet, which top sheet may be attached to the back sheet, (3) an absorbent structure positioned between the top sheet and the back sheet, and (4) an adhesive attachment region, and an optional release liner.

Those skilled in the art will recognize materials suitable for use as the top sheet and back sheet.

Exemplary of materials suitable for use as the top sheet are liquid-permeable materials, such as spunbonded polypropylene or polyethylene having a basis weight of from about 15 to about 25 grams per square meter.

Back sheets often used in disposable absorbent products are generally prepared from liquid-impermeable materials which function to contain liquids, such as water, urine, menses, or blood, within the absorbent core of the disposable absorbent product and to protect bedding and/or a wears' outer garments from soiling. Materials useful as a back sheet in a disposable absorbent product are generally impermeable to liquid but are permeable to vapor. Examples are liquid-impervious materials such as polyolefin films, e.g., polypropylene and polyethylene, as well as vapor-pervious materials, such as microporous polyolefin films, sometimes referred to as breathable films. Laminates of polyethylene films and fabrics, including nonwoven fabrics are included.

A particularly desirable back sheet material is a film comprising a polyolefin polymer such as a linear low density polyethylene and a filler. As used herein a "filler" is meant to include particulates and other forms of materials which can be added to the film polymer extrusion blend and which will not chemically interfere with or adversely affect the extruded film but which are able to be uniformly dispersed throughout the film. When the film is stretched during processing, the filler generally causes a network of holes to be formed in the film. Such holes are generally small enough to prevent the passage of a liquid, but are generally large enough to allow vapor to pass through the holes. Generally the fillers will be in particulate form and usually will have somewhat of a spherical shape with average particle sizes in the range of about 0.1 to about 7 microns. Both organic and inorganic fillers may be used in the practice of the invention provided that they do not interfere with the film formation process. Examples of fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivatives, chitin and chitin derivatives.

A removeable release liner or peelable film covering adhesive attachment region until the device is used can advantageously be used. A silicone-coated film is typically used for such applications. Just prior to use of the device, the proximal release liner is removed to expose the adhesive layer. Thus, the proximal release liner is adapted to be removed from the device and to strip off the adhesive surface with minimal force.

The article has disposed on at least one surface thereon at a predetermined location a radiation cured pressure sensitive hot melt adhesive at a coat weight, e.g., of from about 10 to about 35 $g/m^2$, even more typically of from about 15 to about 25 $g/m^2$. A coating made in accordance with the invention gives an aggressive coating, but still has clean removeability. The adhesive may be coated on the predetermined area of the substrate as a continuous or a discontinuous layer.

While the adhesive attachment region prepared in accordance with the invention are particularly advantageous for use in the construction of disposable articles, non-disposable articles are also encompassed by the invention. Examples of non-disposable articles include photograph album pages for holding and displaying photographs. Other non-limiting examples or articles encompassed by the invention include bed liners, feminine hygiene pads (which include conventional sanitary napkins and panty liners) and adult incontinence pads, dress shields, shoe insoles, bibs, identification badges, price labels, nursing pads, information stickers for clothing, upholstery and the like textile products, wound dressing, shoulder pads, bra pads, double-sided tapes including self supporting double-sided tapes, clothes hangers, stay fresh barrier for food, packaging for cosmetics, cigarettes, and facial tissue. Included within the scope of the invention are articles having at least a front and a back side, which article has a permanent adhesive on one side (e.g., the back side) and a UV-curable adhesive applied in accordance with the invention on the other side (e.g., the front side). Such articles find use, e.g., in permanent attachment of one side of the article to a product, from which article a coupon can be removeably released from the other side of the article upon the purchase of the product.

The adhesive provides secure attachment to a conventional fabric such as cotton, nylon, silk, polyesters and the like, commonly used in the construction of bedding, and clothing including hosiery, and the like, but does not transfer onto adjacent articles (e.g., sanitary napkins or adult incontinent pads) or packaging film when in the package prior to use. Also, when supplied in a tape form with the barrier backing, the barrier backing need not be release coated to facilitate tape unwind, which could interfere with subsequent manufacture of the absorbent pad or sanitary napkin.

The adhesive is coated onto a backing which generally is a thin water impermeable backing, preferably a thermoplastic film, which is most preferably a thin polyethylene polymer, copolymer or blend. The water impermeable backing layer can be treated by, such as but not limited to, corona discharge, to improve adhesion by the adhesive. Further layers can be provided depending on the end use of the repositionable and linerless adhesive/backing laminate. Absorbent layers and liquid permeable cover layers are used for sanitary napkins or adult incontinent pads where the repositionable linerless adhesive would be used to attach to the wearers undergarment keeping the absorbent product in place. With bed liners, the laminate could directly adhere to the bed fabric or cotton sheet with or without a liquid absorbent layer attached to the opposite face of the backing, generally a liquid impermeable film layer.

In one embodiment, the adhesive article comprises an adhesive coated on at least one major surface of a backing having a first and second major surface. Useful backing substrates include, but are not limited to foam, metal, fabric, and various polymer films such as polypropylene, polyamide and polyester. The adhesive may be present on one or both surfaces of the backing. When the adhesive is coated on both surfaces of the backing, the adhesive on each surface can be the same or different.

Backings which can be used in the practice of this invention include, with or without modification, metal foils, metalized polyfoils, composite foils or films containing polytetrafluoroethylene (TEFLON®)-type materials or equivalents thereof, polyether block amide copolymers, polyurethanes, polyvinylidene chloride, nylon, silicone elastomers, rubber-based polyisobutylene styrene, styrene-butadiene and styrene-isoprene copolymers, polyethylene, polyester, and other such materials used in the art of pressure sensitive adhesive articles. Particularly preferred are thermoplastic polymers such as polyolefins, for example polyethylene and polypropylene, and polyesters such as polyethyleneterephthalate.

It has been found that radiation curable hot melt adhesives, such as those comprising UV curable acrylic polymers such as BASF acResin A203UV and tackifiers such as hydrogenated rosin tackifiers exhibit much better positioning performance on a variety of fabrics compared with standard prior art rubber based positioning adhesives ("standard adhesive"). Use of radiation cured hot melt adhesives as positioning adhesives give the following advantages over the standard hot melt positioning adhesives:

Good Bonding to Microfibre Fabrics

Compared with standard hot melt positioning adhesive products, UV cured acrylic hot melt adhesives show much higher bonding strengths to microfibre fabrics. Using a standard prior art adhesive product, the peel value to cotton is high but to microfibre it is extremely low (a tenth to a third of the peel value to cotton), even with a higher coating weight. The UV curable acrylic hot melt adhesive gives similar bond strength to microfibre as to cotton.

Better Bond Strength Balance to Different Fabrics Under Different Testing Conditions It has been shown that UV cured acrylic hot melt adhesive exhibits gives good bond strength in terms of peel value with different fabrics and under different pressing conditions. Whereas for standard hot melt positioning adhesive products, the bond strength is strongly dependent on the types of fabrics and type of pressing conditions, i.e., short contact pressure (rolldown test method), light pressure at a body temperature of 38° C. (150 g at 38° C. for 1 hour) and high pressure at a body temperature of 38° C. for long time (1600 g at 38° C. for 4 hour), which mimics real using conditions, UV curable acrylic hot melt adhesives exhibits very stable bond strength regardless of the types of fabrics and the pressing conditions. The tackified acrylic hot melt adhesives exhibit very high Tan delta values within a wide temperature range and gives very good pressure sensitive properties, i.e., quick and good bonding under light pressure.

Good Ageing Properties

UV curable acrylic hot melt adhesive exhibits excellent long term ageing properties. Long term ageing (at 40° C. and 60° C. for three months) has been carried out and the bond strength is very stable compared to the results before ageing.

Non-staining of Breathable Films

UV acrylic hot melt adhesives, unlike standard hot melt adhesives, do not stain breathable PE films. Breathable PE films are widely used in FemCare products (e.g., sanitary napkins, panty shields) and standard rubber based hot melt adhesive exhibits strong staining on breathable film, particularly at elevated temperature under extreme storage and transportation conditions (typical temperatures are at about 40° C. to 60° C.). In addition, the standard adhesive loses its tackiness and bonding performance after staining. When UV curable acrylic hot melt adhesive was coated onto breathable PE film and left in 40° C. up to 12 weeks after curing, no stain was observed, and the peel values were very stable.

No transfer

No adhesive transfer was observed even under severe pressing conditions (high pressure at long time at high temperature).

Breathability

UV cured acrylic hot melt adhesive exhibits good breathability so it's suitable for skin application. This is a benefit for absorbent articles, on which breathability is always preferred.

Lotion and Fragrance Resistance

While the presence of lotion or fragrance interferes with standard positioning adhesives, leading to less bonding strength to fabrics and adhesive transfer, UV cured acrylic hot melt adhesives exhibit lotion/fragrance resistance.

The invention will be described further in the following examples, which are included for purposes of illustration and are not intended, in any way, to be limiting of the scope of the invention.

EXAMPLES

In the following examples:

Two fabrics were used for testing positioning peel: cotton and microfibre fabrics. The microfibre fabrics sample was supplied by Daleside Dyers & Finishers Ltd. The fabric is made from polyamide fibre with 8% of elastic material (Tactel/Lycra=92/8). The microfibre fabric is black dyed and finished using standard finishing agents (Product no. 9396).

Due to the complicate using conditions of positioning adhesives, three different peel test methods were used to mimic the real end use conditions-rolldown; 250 g weight at 40° C. for 1 hour; and 1.6 kg at 40° C. for 4 hour. The rolldown test is to test the quick bonding of positioning adhesive to fabrics, i.e., the finger pressure to stick the pad to the undergarment. The 250 g weight at 40° C. for 1 hour test is to mimic the bonding development at body temperature with certain pressure, whereas the 1.6 kg weight at 40° C. for 4 hours is to mimic the extreme conditions-higher pressure at body temperature for 4 hours. The 1.6 kg weight test is to identify overbonding and adhesive transfer which is not acceptable on the final products.

In peel tests, a 25 mm×100 mm adhesive sample was cut and gently put on top of cut microfibre fabrics (60 mm×100 mm) and then subjected to one or more the following press conditions:

Rolldown test: 2 kg roller rolls down (forth and back) at 300 mm/min. After rolldown, peel value is measured immediately. Peel test method number: 37 (500 mm/min crosshead speed).

250 g weight at 40° C. for 1 hour: five specimens were piled and put on glass plate with 250 g weight on top. After 1 hour in 40° C. oven, the sample was taken out and left in CT lab for 15 minutes before peel testing. Peel test method number: 37 (500 mm/min crosshead speed).

1600 g weight at 40° C. for 4 hour: five specimens were piled and put on glass plate with 1600 g weight on top. After 4 hours in 40° C. oven, the sample was taken out and left in CT lab for 15 minutes before peel testing. Peel test method number: 37 (500 mm/min crosshead speed).

Example 1

An adhesive containing 80% AC203 UV curable acrylic polymer and 20% Foral 85 as tackifier (Sample 1), was compared to a standard prior art positioning adhesive based on styrene block copolymers (Comparative Sample A, available from National Starch and Chemical Company (DF-645)). This latter adhesive exhibits good bonding to cotton, but poor bonding to microfibre.

Since stable peeling value with long term ageing is required for positioning adhesives, 3 months ageing peel test were carried out at 40° C. and 60° C.

The ageing test was conducted as follows: Using a small coater, two different coating weights of Sample 1 (100 mJ/cm$^2$ and 150 mJ/cm$^2$) were coated onto PE films. The coated samples were cured at UVB 50 mJ/cm$^2$. It was found that 50 mJ/cm$^2$ was high enough to give enough cohesion strength and no transfer was observed.

For the ageing test, both 15 gsm and 20 gsm samples cured at 100 mJ/cm$^2$ were put into plastics bags and were left in 40° C. and 60° C. oven for 1 week, 4 weeks, 8 weeks, and 12 weeks respectively. After ageing, the samples were taken out and the peel test was carried out.

Two sample preparation methods were used:
Rolldown 300 mm/min for 1 cycle (forth and back), and
250 g wt 40° C. for 1 hour and standard cotton and microfibre fabrics.

The peel value to cotton and microfibre was determined on Instron at 500 mm/min crosshead speed.

The average peel values (g/25 mm) for the 15 gsm and 20 gsm samples with different ageing times up to 3 months are shown in Table 1 and 2, respectively.

TABLE 1

| Sample 1 15 gsm/100 mJ/cm$^2$ UVB | Cotton (rolldown) | Microfibre (rolldown) | Cotton (250 g wt) | Microfibre (250 g wt) |
| --- | --- | --- | --- | --- |
| Initial | 129.7 | 149.7 | 87 | 83.1 |
| 40° C. for 1 week | 141.7 | 156.7 | 86.5 | 86.8 |
| 40° C. for 4 week | 121.6 | 145.1 | 89.8 | 79.1 |

TABLE 1-continued

| Sample 1 15 gsm/100 mJ/cm$^2$ UVB | Cotton (rolldown) | Microfibre (rolldown) | Cotton (250 g wt) | Microfibre (250 g wt) |
| --- | --- | --- | --- | --- |
| 40° C. for 8 week | 122.5 | 144.8 | 88.2 | 80.3 |
| 40° C. for 12 week | 132.4 | 147 | 80.2 | 79.6 |
| Initial | 129.7 | 149.7 | 87 | 83.1 |
| 60° C. for 1 week | 115.3 | 139.5 | 85.9 | 86.4 |
| 60° C. for 4 week | 113.1 | 134 | 75.4 | 88.7 |
| 60° C. for 8 week | 112.4 | 130.8 | 80.2 | 81.4 |
| 60° C. for 12 week | 111.6 | 135.9 | 69.5 | 78.1 |

TABLE 2

| Sample 1 20 gsm/100 mJ/cm$^2$ UVB | Cotton (rolldown) | Microfibre (rolldown) | Cotton (250 g wt) | Microfibre (250 g wt) |
| --- | --- | --- | --- | --- |
| Initial | 201.4 | 213 | 132.2 | 117.1 |
| 40° C. for 1 week | 198.6 | 179 | 147.5 | 121.3 |
| 40° C. for 4 week | 190.7 | 199.1 | 106.6 | 141.1 |
| 40° C. for 8 week | 185.4 | 187.5 | 110.2 | 137.8 |
| 40° C. for 12 week | 201.2 | 212.8 | 131.3 | 121.5 |
| Initial | 201.4 | 213 | 132.2 | 117.1 |
| 60° C. for 1 week | 161.6 | 200.8 | 123.2 | 132.5 |
| 60° C. for 4 week | 183 | 198.7 | 115.3 | 118.1 |
| 60° C. for 8 week | 178.3 | 195.4 | 109.5 | 113.3 |
| 60° C. for 12 week | 174.6 | 199.6 | 106.9 | 127.9 |

FIGS. 1 and 2 compare of peel value to cotton and microfibre with the 15 gsm sample and 20 gsm sample. It is clear seen that there is no peel value change under 40° C. ageing up to three months. Sample 1 gives very stable peel value to cotton and microfibre with both coating weights. This is better than rubber based positioning adhesive of Sample A.

Sample A was coated on standard PE with 20 gsm. It was observed that, the peel value drops about 20% after 3 weeks ageing. When the sample was aged at 60° C., peel to cotton is slightly decreased by about 10% after 1 week and then stable even after 12 weeks ageing but no peel drop was observed for microfibre.

When coated on a breathable PE film, peel drop of Sample A can reach 80% after a few weeks of ageing at 40° C. due to staining of the adhesive. In contrast, as shown the below Example 2, Sample 1 does not stain breathable PE films.

Example 2

Breathable PE film has become more and popular as back sheet for FemCare products due to the breathability of this material. As noted above, one big issue for standard rubber based positioning adhesive is staining on breathable PE film. It was found that the standard positioning adhesive Sample A created serious staining on breathable PE films. This causes the peel strength to significantly drop and, in addition, has a detrimental influence the appearance of the final product. The staining is mainly due to the porous structure of film and the filler's absorbance and the low molecular parts present in the adhesive (e.g., oil).

To show that UV curable acrylic hot melt adhesives do not stain breathable films, Sample 1 was been coated onto breathable film. Un-aged and aged peel strength was measured.

Sample 1 was coated onto breathable PE film (a commercially available breathable film known to stain) and standard PE on small coater. Coating weight was 20 gsm. The coating conditions were 20 m/min, tank/head temperature: 155° C., coating onto silicone paper and then transfer to PE film. Sample A was also used as control.

Samples were cured at 50 and 100 mj/cm2 UVB.

Both coated samples were aged in a 40° C. oven for 5 weeks to 12 weeks. The staining was checked every week. The staining at room temperature (RT) was also checked very week.

Ageing Peel:

Three peel test methods were used to measure the peel strength to the standard fabrics, i.e., rolldown 300 mm/min for 1 cycle (forth and back); 250 g wt 40oC. for 1 hour and 1.6 kg wt 40oC. for 4 hours.

Standard cotton and microfibre fabrics were used.

The peel value to cotton and microfibre was determined on Instron at 500 mm/min crosshead speed.

The average aged and unaged peel results (g/25 mm) are listed t in the following Table 3.

TABLE 3

|  |  | Roll down | | 250 g wt 40° C. 1 h | | 1.6 kg wt 40° C. 4 h | |
| --- | --- | --- | --- | --- | --- | --- | --- |
|  |  | Cotton (rolldown) | Microfibre (rolldown) | Cotton (250 g wt) | Microfibre (250 g wt) | Cotton (1.6 kg wt) | Microfibre (1.6 kg wt) |
| Sample A | RT for 5 weeks | 197.8 | 44 | 72.1 | 83.7 | 132 | 98.9 |
| 20 gsm standard PE | 40° C. for 5 week | 149.6 | 30.7 | 49.2 | 69.7 | 116.5 | 147 |
|  | 40° C. for 12 week | 149.6 | 36.9 | 60.1 | 66.7 | 112.6 | 147.7 |
| Sample A | RT for 5 weeks | 175.1 | 21.1 | 49.1 | 54.7 | 103.7 | 84.2 |
| 20 gsm breathable PE | 40° C. for 5 week | 10 | 3.6 | 16.2 | 6.5 | 28.9 | 48.1 |
| Sample 1 20 gsm standard PE 50 mJ/cm2 UVB | RT for 5 weeks | 264.8 | 235.1 | 157.3 | 189.9 | 267.7 | 285.7 |
| Sample 1 20 gsm standard PE 90 mJ/cm2 UVB | RT for 5 weeks | 242.1 | 222 | 141.1 | 173.5 | 207.1 | 208.9 |
| Sample 1 20 gsm breathable PE 50 mJ/cm2 UVB | RT for 5 weeks | 251.9 | 239 | 170.2 | 210.1 | 205.8 | 281.9 |
|  | 40° C. for 5 week | 263.6 | 279.7 | 146.7 | 224.8 | 233.9 | 285 |
|  | 40° C. for 12 week | 264.0 | 266.6 | 146.8 | 208.1 | 234.2 | 300.0 |
| Sample 1 | RT for 5 weeks |  |  |  |  |  |  |
| 20 gsm breathable PE | 40° C. for 5 week | 258.6 | 264.4 | 128.9 | 177.9 | 178.3 | 278.5 |
| 100 mJ/cm2 UVB | 40° C. for 12 week | 249.3 | 254.6 | 136.6 | 177.9 | 229.1 | 304.0 |

For Sample A coated on to breathable film, heavy staining was be observed after 1 week at 40° C. oven. After 1 week, the staining does not change much. At room temperature, the staining was much slower but obvious staining still could be observed after 4 or 5 weeks.

For the Sample 1 coated samples, the cured samples were aged in oven at 40° C. for 10 weeks, no staining was observed on breathable films. This confirmed that cured Sample 1 will not stain breathable films.

The invention claimed is:

1. A disposable absorbent article comprising an adhesive attachment region for positioning the article to a fabric substrate, said attachment region comprising a cured ultraviolet curable acrylic hot melt adhesive composition, said composition comprising an acrylic polymer obtained from a C4 to C8 alkylacrylate comprising (a) a covalently bonded photoinitiator and (b) a tackifier which is a hydrogenated rosin ester and/or a rosin acid.

2. The article of claim 1 wherein the ultraviolet curable acrylic hot melt adhesive composition comprises an ultraviolet curable acrylic polymer.

3. The article of claim 2 wherein the ultraviolet curable acrylic polymer comprises a 2-ethylhexyl acrylate that has bonded to it a pendant benzophenone group.

4. The article of claim 1 which is a disposable absorbent product.

5. The article of claim 4, which disposable absorbent product comprises a liquid-permeable top sheet, a liquid-impermeable back sheet, which top sheet may be attached to the back sheet, an absorbent structure positioned between the top sheet and the back sheet, and an adhesive attachment region positioned on said back sheet.

6. The article of claim 5 wherein said back sheet comprises a breathable film.

7. The article of claim 5 further comprising a release liner.

8. The article of claim 7 which article is a feminine hygiene pad.

9. A feminine hygiene pad comprising a liquid-permeable top sheet, a liquid-impermeable back sheet, which top sheet may be attached to the back sheet, an absorbent structure positioned between the top sheet and the back sheet, and an adhesive attachment region positioned on said back sheet, said adhesive attachment region comprising a cured ultraviolet curable acrylic hot melt pressure sensitive adhesive, said ultraviolet curable acrylic hot melt pressure sensitive adhesive comprising (a) an acrylic polymer obtained from a C4 to C8 alkylacrylate comprising a covalently bonded photoinitiator and (b) a tackifier which is a hydrogenated rosin ester and/or a rosin acid.

10. The feminine hygiene pad of claim 9 wherein the back sheet comprises a breathable polyethylene film.

* * * * *